United States Patent
Liu et al.

(10) Patent No.: US 7,052,460 B2
(45) Date of Patent: May 30, 2006

(54) SYSTEM FOR PRODUCING AN ULTRASOUND IMAGE USING LINE-BASED IMAGE RECONSTRUCTION

(75) Inventors: Godwin Liu, Burlington (CA); Chris Aleksandr White, Toronto (CA); Randy Hendriks, Toronto (CA); Stuart Foster, Toronto (CA); Tom Little, Toronto (CA)

(73) Assignee: VisualSonics Inc., Toronto (CA)

( * ) Notice: Subject to any disclaimer, the term of this patent is extended or adjusted under 35 U.S.C. 154(b) by 107 days.

(21) Appl. No.: 10/736,232

(22) Filed: Dec. 15, 2003

(65) Prior Publication Data

US 2004/0236219 A1    Nov. 25, 2004

Related U.S. Application Data

(60) Provisional application No. 60/468,958, filed on May 9, 2003, provisional application No. 60/468,956, filed on May 9, 2003, provisional application No. 60/470,234, filed on May 14, 2003.

(51) Int. Cl.
A61B 8/00    (2006.01)

(52) U.S. Cl. .................................... 600/443

(58) Field of Classification Search ........ 600/400–449; 73/625–626; 128/916
See application file for complete search history.

(56) References Cited

U.S. PATENT DOCUMENTS

| | | | |
|---|---|---|---|
| 4,413,521 A | | 11/1983 | Van Kemenade |
| 4,888,694 A | | 12/1989 | Chesarek |
| 4,991,589 A | * | 2/1991 | Hongo et al. ............... 600/455 |
| 5,099,847 A | | 3/1992 | Powers et al. |
| 5,390,674 A | | 2/1995 | Robinson et al. |
| 5,579,771 A | * | 12/1996 | Bonnefous ................... 600/450 |
| 5,797,846 A | | 8/1998 | Seyed-Bolorforosh et al. |
| 5,940,123 A | | 8/1999 | Daigle et al. |
| 6,099,473 A | | 8/2000 | Liu et al. |
| 6,123,670 A | | 9/2000 | Mo et al. |
| 6,139,500 A | * | 10/2000 | Clark ........................ 600/443 |
| 6,193,662 B1 | | 2/2001 | Hwang |
| 6,200,267 B1 | | 3/2001 | Burke |
| 6,350,238 B1 | | 2/2002 | Olstad et al. |
| 6,494,838 B1 | | 12/2002 | Cooley et al. |
| 6,544,175 B1 | * | 4/2003 | Newman ..................... 600/437 |
| 6,638,220 B1 | | 10/2003 | Satoh |
| 2002/0045824 A1 | | 4/2002 | Cooley et al. |
| 2002/0045825 A1 | | 4/2002 | Liu et al. |
| 2003/0120152 A1 | | 6/2003 | Omiya et al. |
| 2003/0171668 A1 | | 9/2003 | Tsujino et al. |

(Continued)

FOREIGN PATENT DOCUMENTS

WO        WO 98/40014        9/1998

(Continued)

OTHER PUBLICATIONS

Foster et al., "High frequency ultrasound imaging: from man to mouse", IEEE Ultrasonics Symposium. 2:1633-1638 (2002).

(Continued)

Primary Examiner—Francis J. Jaworski
(74) Attorney, Agent, or Firm—Needle & Rosenberg, P.C.

(57) ABSTRACT

A system for developing an ultrasound image, comprises a scan head having a transducer capable of generating ultrasound energy at a frequency of at least 20 megahertz (MHz), and a processor for receiving ultrasound energy and for generating an ultrasound image at an effective frame rate of at least 200 frames per second (fps) using scan line based image reconstruction.

26 Claims, 10 Drawing Sheets

U.S. PATENT DOCUMENTS

| | | |
|---|---|---|
| 2004/0006271 A1 | 1/2004 | Golland et al. |
| 2004/0102704 A1 | 5/2004 | Tsujita et al. |
| 2004/0122319 A1 | 6/2004 | Mehi et al. |
| 2004/0267124 A1 | 12/2004 | Roundhill |
| 2005/0010111 A1 | 1/2005 | Kristoffersen et al. |
| 2005/0049498 A1 | 3/2005 | Roche et al. |
| 2005/0124894 A1 | 6/2005 | Puech |
| 2005/0197572 A1 | 9/2005 | Williams et al. |
| 2005/0203407 A1 | 9/2005 | Yoshihara et al. |

FOREIGN PATENT DOCUMENTS

| | | |
|---|---|---|
| WO | WO 2004034694 A2 | 4/2004 |

OTHER PUBLICATIONS

Turnbull et al., "In vivo ultrasound biomicroscopy in developmental biology" Trends in Biotechnology, Elsevier Publications, Cambridge, GB 20(8):S29-S33 (2002).

* cited by examiner

Time stamp each line relative to ecg signal

SYSTEM FOR PRODUCING AN ULTRASOUND IMAGE USING LINE-BASED IMAGE RECONSTRUCTION

CROSS-REFERENCE TO RELATED APPLICATIONS

This application claims priority to and the benefit of U.S. Provisional Application No. 60/468,958, entitled "SCAN HEAD FOR ULTRASOUND IMAGING SYSTEM," filed on May 9, 2003; U.S. Provisional Application No. 60/468,956, entitled "REMOVABLE ACOUSTIC WINDOW," filed on May 9, 2003; and U.S. Provisional Application No. 60/470,234, entitled "METHOD AND APPARATUS FOR OBTAINING AN ULTRASOUND IMAGE," filed on May 14, 2003, all of which are incorporated in this document by reference.

BACKGROUND

The present invention relates to producing an ultrasound image using line based image reconstruction.

Ultrasound imaging has become important for the medical diagnosis and understanding of stages of cardiovascular diseases such as strokes and heart attacks. Because of the rapid motions of a beating heart and other rapidly moving anatomy, special techniques have been designed to capture images rapidly to provide an accurate visual representation of rapidly moving anatomy. Of particular interest are the valves of the heart and the precise motions of the heart muscle wall. Also of interest are high quality representations and analyses of blood flow patterns.

The electro cardiogram (or "ECG", and sometimes referred to as "EKG") is a technique used to monitor electrical signals originating from the heart during its movement. Electrical signals originating from the heart may be detected at the surface of the skin in the vicinity of the heart. The ECG signal can be used to track the cycle of heart function. Various "ECG gating" or "ECG synchronization" techniques have been developed to improve ultrasound image acquisition by making use of simultaneously acquired ECG signals to coordinate timing of image acquisition relative to the cardiac cycle.

Ultrasound ECG techniques have focused on the acquisition of complete image frames at specific time intervals on the ECG wave form. By 'triggering' the start of ultrasound frame acquisition at a specified time relative to each heart beat, and acquiring image after image at the same point in the cardiac cycle, systems can effectively freeze the motion of the heart using a "strobing" principle. Systems also begin image acquisition at a specified interval from a standard point in the ECG wave form, such that two sets of moving heart images can be synchronized and compared, beginning from the same point in the cardiac cycle. ECG gating on a frame by frame basis is a good technique so long as the acquisition time for any given frame is relatively short compared to the movements depicted. A good analogy is a photograph with a short exposure time. The faster the motion, the shorter the exposure time that is required to accurately capture the structure in motion. Too long an exposure time results in a distorted image.

ECG based frame reordering has also been attempted to visualize rapidly moving anatomy. In a frame based reordering technique, a moderate increase in frame rate can be achieved by collecting data frames, and reordering the data frames by comparing the start time of each frame acquisition to the ECG signal. Frames can then be replayed at a faster rate. However, this technique does not yield a true representation of the rapidly moving anatomy because the finite time required to acquire a frame causes data overlap between frames. Thus each "stop motion" frame may not have complete time independence.

These existing ECG based imaging techniques have worked adequately well in the area of human echocardiography, the use of ultrasound for examination of the heart, but are insufficient for higher frame rate applications such as imaging rapidly moving structures in small animals. For example, the heart rate of a small animal, such as a mouse, is significantly faster than the heart rate of a human. The assumption that a frame acquisition is relatively instantaneous no longer holds true at faster rates, therefore gating ultrasound acquisition on a frame basis is not useful for imaging such rapidly moving anatomy.

SUMMARY

In one aspect, the invention is a system for developing an ultrasound image, comprising a scan head having a transducer capable of generating ultrasound energy at a frequency of at least 20 megahertz (MHz), and a processor for receiving ultrasound energy and for generating an ultrasound image at an effective frame rate of at least 500 frames per second (fps) using scan line based image reconstruction.

Related methods of operation are also provided. Other systems, methods, features, and advantages of the invention will be or become apparent to one with skill in the art upon examination of the following figures and detailed description. It is intended that all such additional systems, methods, features, and advantages be included within this description, be within the scope of the invention, and be protected by the accompanying claims.

BRIEF DESCRIPTION OF THE FIGURES

The invention can be better understood with reference to the following figures. The components within the figures are not necessarily to scale, emphasis instead being placed upon clearly illustrating the principles of the invention. Moreover, in the figures, like reference numerals designate corresponding parts throughout the different views.

DETAILED DESCRIPTION

The system for producing an ultrasound image using line based image reconstruction provides an ultrasound image having an effective frame rate in excess of 500 frames per second. The system incorporates an ECG based technique that enables significantly higher time resolution than what was previously available, thus allowing the accurate depiction of a rapidly moving structure, such as a heart, in a small animal, such as a mouse, rat, rabbit, or other small animal, using ultrasound (and ultrasound biomicroscopy). Biomicrosopy is an increasingly important application due to recent advances in biological, genetic, and biochemical techniques, which have advanced the mouse as a desirable test subject for the study of diseases, including the cardiovascular diseases.

In one aspect, the system for producing an ultrasound image using line based image resonstruction addresses specifically the need to image and analyze the motions of the heart of a small animal with proportionally relevant time and detail resolution. Such imaging is also applicable to imaging small structures within a human body. It also applies to other ultrasound imaging applications where effective frame rates greater than, for example, 200 frames per second are desired.

The human heart during rest beats regularly at a typical rate of 60–90 bpm (beats per minute). With clinical ultrasound, physicians generally desire 100 frames per heart beat to accurately depict motion, resulting in imaging frame rates of approximately 100 fps (frames per second). An adult mouse heart under similar conditions typically beats at a rate of 300–600 bpm. Therefore, to achieve 100 frames per heart beat, the desired imaging frame rate is approximately at or above 500–1000 fps, or higher.

Ultrasound images are formed by the analysis and amalgamation of multiple pulse echo events. An image is formed, effectively, by scanning regions within a desired imaging area using individual pulse echo events, referred to as "A-Scans", or ultrasound "lines." Each pulse echo event requires a minimum time for the acoustic energy to propagate into the subject and to return to the transducer. The image is completed by "covering" the desired image area with a sufficient number of scan lines, referred to as "painting in" the desired imaging area so that sufficient detail of the subject anatomy can be displayed. The number of and order in which the lines are acquired can be controlled by the ultrasound system, which also converts the raw data acquired into an image. Using a combination of hardware electronics and software instructions in a process called "scan conversion," or image construction, the ultrasound image obtained is rendered so that a user viewing the display can view the subject being imaged.

To decrease the amount of time required to obtain an image, the image is subdivided into regions, where each region corresponds to a single scan line. ECG signals acquired during the ultrasound scanning operation are used to time register individually the subdivided data (i.e., the individual pulse-echo events," or "raw data" associated with each scan line). A scan conversion mechanism utilizes the ultrasound lines, which are time registered with the ECG signal, to develop an image having an effective frame rate significantly greater that the frame rate that may be obtained in real-time. A sequential series of image frames is reconstructed from the pool of time and position registered raw data to reconstruct a very high precision (i.e., high frame rate) representation of the rapidly moving structure.

Figure 1:
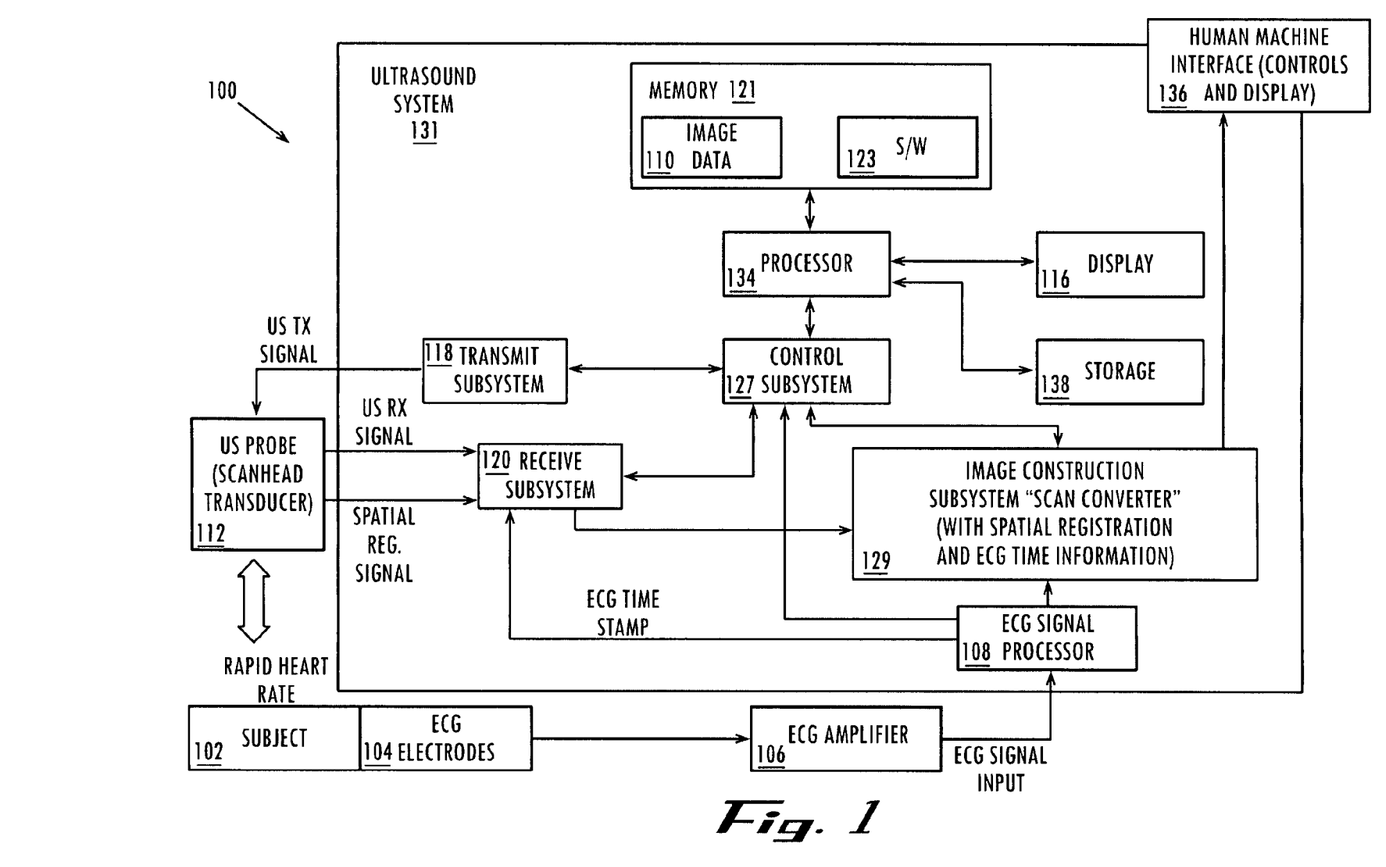
FIG. 1 is a block diagram of an ultrasound imaging system.

FIG. 1 is a block diagram illustrating an imaging system 100. The system 100 operates on a subject 102. An ultrasound probe 112 is placed in proximity to the subject 102 to obtain image information. The ultrasound probe generates ultrasound energy at high frequencies, such as but not limited to greater than 20 MHz and including 25 MHz, 30 MHz, 35 MHz, 40 MHz, 45 MHz, 50 MHz, 55 MHz, 60 MHz and higher. Further, ultrasound operating frequencies significantly greater than those mentioned above are also contemplated. The subject 102 is connected to electrocardiogram (ECG) electrodes 104 to obtain a cardiac rhythm from the subject 102. The cardiac signal from the electrodes 104 is transmitted to an ECG amplifier 106 to condition the signal for provision to an ultrasound system 131. It is recognized that a signal processor or other such device may be used instead of an ECG amplifier to condition the signal. If the cardiac signal from the electrodes 104 is suitable, then use of an amplifier 106 or signal processor could be avoided entirely.

The ultrasound system 131 includes a control subsystem 127, an image construction subsystem 129, sometimes referred to as a "scan converter", the transmit subsystem 118, the receive subsystem 120 and the user input device 136. The processor 134 is coupled to the control subsystem 127 and the display 116 is coupled to the processor 134. A memory 121 is coupled to the processor 134. The memory 121 can be any type of computer memory, and is typically referred to as random access memory "RAM," in which the software 123 of the invention executes. The software 123 controls the acquisition, processing and display of the ultrasound data allowing the ultrasound system 131 to display a high frame rate image so that movement of a rapidly moving structure may be imaged. The software 123 comprises one or more modules to acquire, process, and display data from the ultrasound system 131. The software comprises various modules of machine code which coordinate the ultrasound subsystems, as will be described below. Data is acquired from the ultrasound system, processed to form complete images, and then displayed to the user on a display 116. The software 123 allows the management of multiple acquisition sessions and the saving and loading of these sessions. Post processing of the ultrasound data is also enabled through the software 123.

The system for producing an ultrasound image using line-based image reconstruction can be implemented using a combination of hardware and software. The hardware implementation of the system for producing an ultrasound image using line based image reconstruction can include any or a combination of the following technologies, which are all well known in the art: discrete electronic components, a discrete logic circuit(s) having logic gates for implementing logic functions upon data signals, an application specific integrated circuit having appropriate logic gates, a programmable gate array(s) (PGA), a field programmable gate array (FPGA), etc.

The software for the system for producing an ultrasound image using line based image reconstruction comprises an ordered listing of executable instructions for implementing logical functions, and can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM), a read-only memory (ROM), an erasable programmable read-only memory (EPROM or Flash memory) (magnetic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

The memory 121 can include the image data 110 obtained by the ultrasound system 100. A computer readable storage medium 138 is coupled to the processor for providing instructions to the processor to instruct and/or configure processor to perform steps or algorithms related to the operation of the ultrasound system 131, as further explained below. The computer readable medium can include hardware and/or software such as, by way of example only, magnetic disks, magnetic tape, optically readable medium such as CD ROM's, and semiconductor memory such as PCMCIA cards. In each case, the medium may take the form of a portable item such as a small disk, floppy diskette, cassette, or it may take the form of a relatively large or immobile item such as hard disk drive, solid state memory card, or RAM provided in the support system. It should be noted that the above listed example mediums can be used either alone or in combination.

The ultrasound system 131 can include a control subsystem 127 to direct operation of various components of the ultrasound system 131. The control subsystem 127 and related components may be provided as software for instructing a general purpose processor or as specialized electronics in a hardware implementation. The ultrasound system 131 includes an image construction subsystem 129 for converting the electrical signals generated by the received ultrasound echoes to data that can be manipulated by the processor 134 and that can be rendered into an image on the display 116. The control subsystem 127 is connected to a transmit subsystem 118 to provide an ultrasound transmit signal to the ultrasound probe 112. The ultrasound probe 112 in turn provides an ultrasound receive signal to a receive subsystem 120. The receive subsystem 120 also provides signals representative of the received signals to the image construction subsystem 129. The receive subsystem 120 is also connected to the control subsystem 127. The scan converter 32 is directed by the control subsystem 127 to operate on the received data to render an image for display using the image data 110.

The ultrasound system 131 can include an ECG signal processor 108 configured to receive signals from the ECG amplifier 106. The ECG signal processor 108 provides various signals to the control subsystem 127. The receive subsystem 120 also receives an ECG time stamp from the ECG signal processor 108. The receive subsystem 120 is connected to the control subsystem 127 and an image construction subsystem 129. The image construction subsystem 129 is directed by the control subsystem 127.

The ultrasound system 131 transmits and receives ultrasound data through the ultrasound probe 112, provides an interface to a user to control the operational parameters of the imaging system 100, and processes data appropriate to formulate still and moving images that represent anatomy and/or physiology. Images are presented to the user through the interface display 116.

The human-machine interface 136 of the ultrasound system 131 takes input from the user, and translates such input to control the operation of the ultrasound probe 106. The human-machine interface 136 also presents processed images and data to the user through the display 116.

The software 123 in cooperation with the image construction subsystem 129 operate on the electrical signals developed by the receive subsystem 120 to develop a high frame-rate ultrasound image that can be used to image rapidly moving anatomy of the subject 102.

Figure 2A:
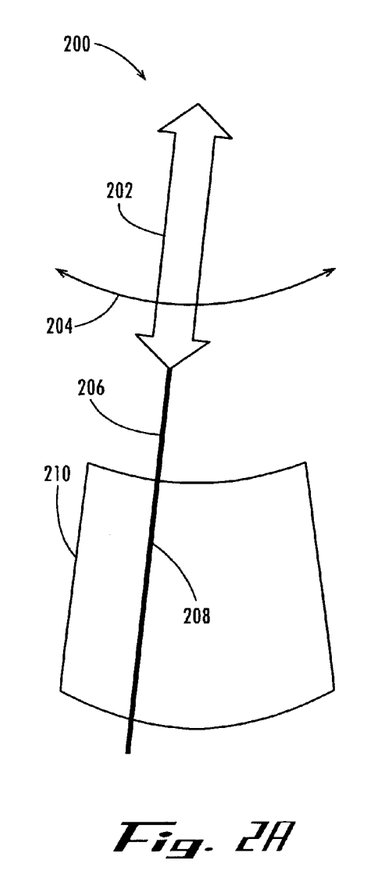
FIGS. 2A and 2B are schematic representations depicting methods of ultrasound imaging.
Figure 2B:
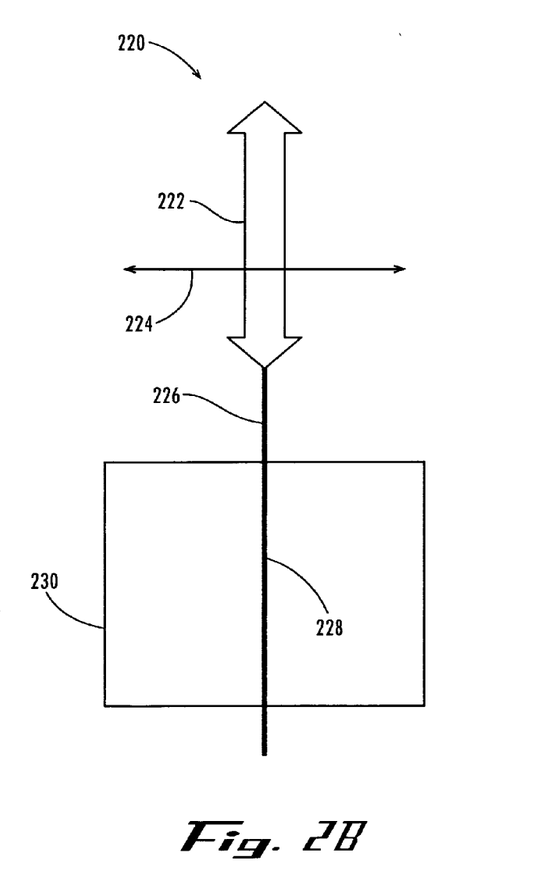

FIGS. 2A and 2B are schematic representations depicting methods of ultrasound imaging. In FIG. 2A, the operation of the ultrasound probe 112 in a sector format scan is illustrated generally. In FIG. 2A, use of the ultrasound probe 112 to obtain a sector format image is shown by the numeral 200. An ultrasound signal propagates in direction 202 projecting a "line" 206 of ultrasound energy. The ultrasound probe 112 moves along an arc 204. The ultrasound signal thus images, or "paints in," a portion 208 of a sector format image 210.

An alternative format of image is shown in FIG. 2A by the numeral 220. The ultrasound probe 112 propagates a signal in direction 222 projecting a "line" 226 of ultrasound energy. The position of the ultrasound probe 112 moves along a line 224. The ultrasound signal thus images, or "paints in," a portion 228 of rectangular format image 230.

It will be recognized that many other formats of images may be used with the ultrasound probe 112. The above examples illustrate the general principles that are used for other formats of images. Any technique that acquires spatially limited data may be used, including painting in a region, two-dimensional, and three-dimensional imaging.

The control subsystem 127 coordinates the operation of the ultrasound probe 112, based on user selected parameters, and other system inputs.

The control subsystem 127 ensures that data is acquired at each spatial location, and for each time window relative to the ECG signal. Therefore, a full data set includes raw data for each time window along the ECG signal, and for each spatial portion of the image frame. It is recognized that an incomplete data set may be used with appropriate interpolation between the values in the incomplete data set being used to approximate the complete data set.

The transmit subsystem 118 generates ultrasound pulses based on user selected parameters. The ultrasound pulses are sequenced appropriately by the control subsystem 127 and are applied to the probe 112 for transmission toward the subject 102.

The receive subsystem 120 records the echo data returning from the subject 102, and processes the ultrasound echo data based on user selected parameters. The receive subsystem 120 also receives a spatial registration signal from the probe 112 and provides position and timing information related to the received data to the image construction subsystem 129.

Figure 3A:
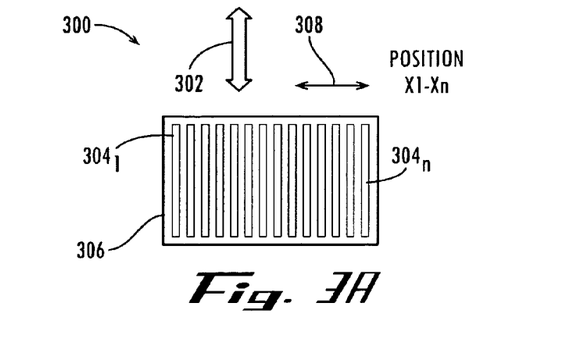
FIGS. 3A through 3E are schematic diagrams illustrating the system for generating an ultrasound image using line based image reconstruction.

FIGS. 3A through 3E are schematic diagrams illustrating the operation of the system for producing an ultrasound image using line-based image reconstruction. The operation described below may be implemented using the software 123 to control the operation ultrasound system 131. FIG. 3A shows an ultrasound frame 300. The ultrasound probe 112 (FIG. 1) produces an ultrasound signal along line 302. FIG. 3A shows an exemplary representative signal which shows the general form of ultrasound signals. Each position of the ultrasound probe 112 along the line 308 provides a scan line 304 in the rectangular format image frame 306. The scan lines are labelled $304_1$ through $304_n$, depending on the number of lines per frame.

Figure 3B:
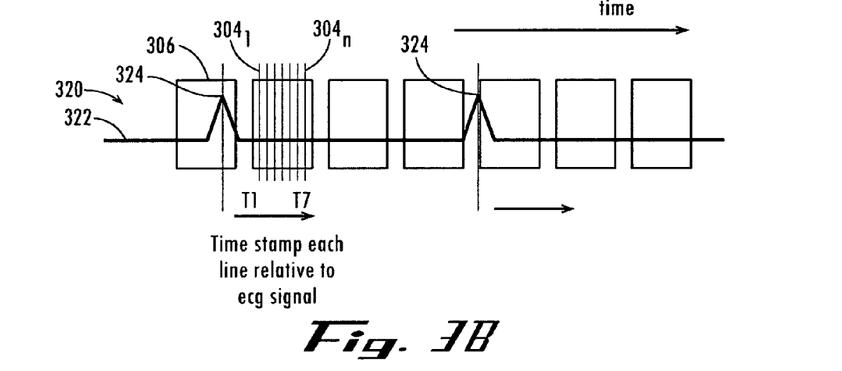
Figure 3C:
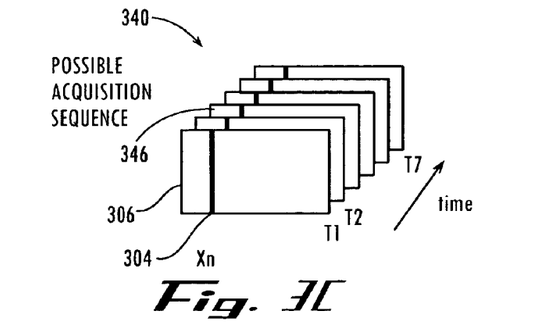
Figure 3D:
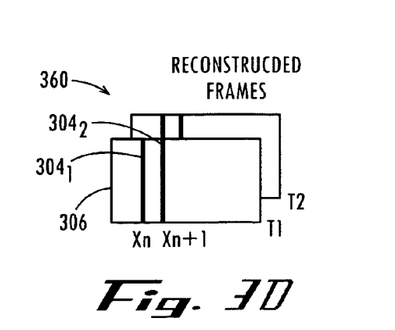
Figure 3E:
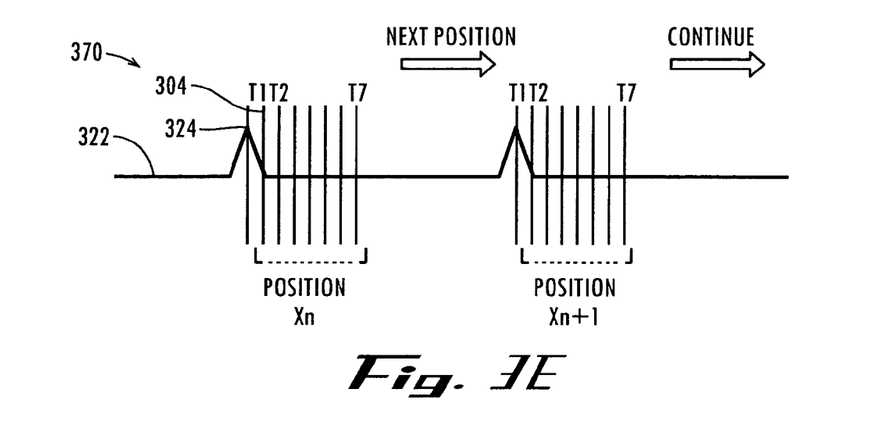

FIG. 3B is a schematic diagram 320 showing a plurality of image frames 306 along a cardiac rhythm trace 322. The portions 326a and 326b of the cardiac rhythm trace 322 are referred to as an "R" wave. By monitoring the ECG signal using the ECG signal processor 108 (FIG. 1), a specific point 324 in the cardiac rhythm trace 322 may be identified, and a time stamp obtained for each line 304 relative to and offset from the point 324. The point 324 is referred to as the peak of the R wave. Thus, by collecting the same line 304 in frames 306, with each line 304 in each frame having the same offset from the point 324, an acquisition sequence 340, as shown in FIG. 3B, is obtained. The acquisition sequence 340 comprises frames 306 in which the same scan line 304 is collected, thus yielding a full cycle of the heart between points 324. As shown in FIG. 3D, the frames 306 may be reconstructed by reassembling multiple scan lines $304_1$ and $304_2$, for example. Each position $X_n$, $X_{n+1}$ of the ultrasound probe 112 yields lines at times T1, T2, . . . , T7 shown in FIG. 3E.

During image acquisition, the image construction subsystem 129 records as input all of the raw data associated with the scan lines 304, including position and ECG-time registration information for each line. When an amount of data sufficient to provide an acceptable image has been collected, the control subsystem 127 sends a signal to the image construction subsystem 129 initiating a reconstruction sequence in which the raw data for each scan line 304 is assembled into a complete image, by collecting sub-regions (i.e., individual scan lines 304) of the image. The sub-regions are temporally relative to a specific point 324 in the ECG cycle and generally correspond to the cardiac cycle from R wave to R wave. The assembly of the individual scan lines over a series of image frames results in a sequential time-series of complete image frames. When viewed, the time-series of constructed image frames appears to have an effective frame rate in excess of 500 fps and appears as a smooth and accurate depiction of rapidly moving structures.

The minimum time of frame acquisition represented is thus the maximum raw time required to obtain each raw data scan line 304, rather than the time required to obtain an entire image frame 306, thus providing an effective frame rate much greater that what would be obtained using real-time or frame-based image reconstruction.

Figure 4:
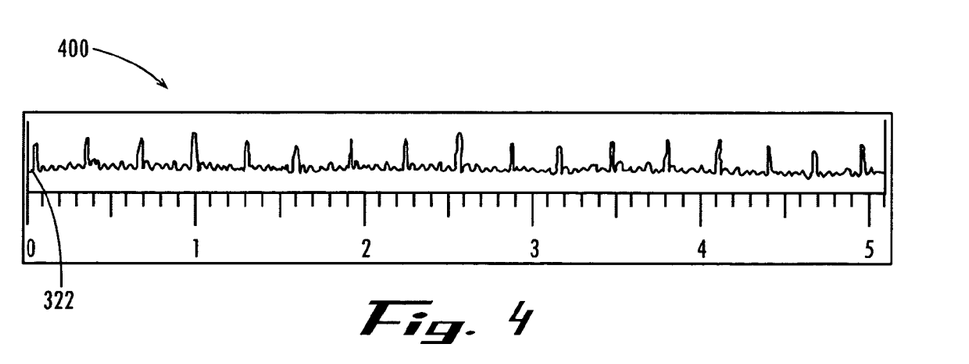
FIG. 4 is an exemplary electrocardiogram signal used in the system of FIG. 1.

An exemplary ECG signal is shown in FIG. 4 by the numeral 400. The ECG signal is represented by the trace 322. The ECG signal processing module 108 (FIG. 1) of the ultrasound system 131 automatically detects, using peak detection of the R-wave pulse, a fixed and repeatable point (324 in FIG. 3B) on the ECG signal trace 322 from which the scan lines 304 are referenced in time. This automatically detects a point in time which is used as the origin for relative ECG time stamps for each element of raw data associated with each can line.

Figure 5:
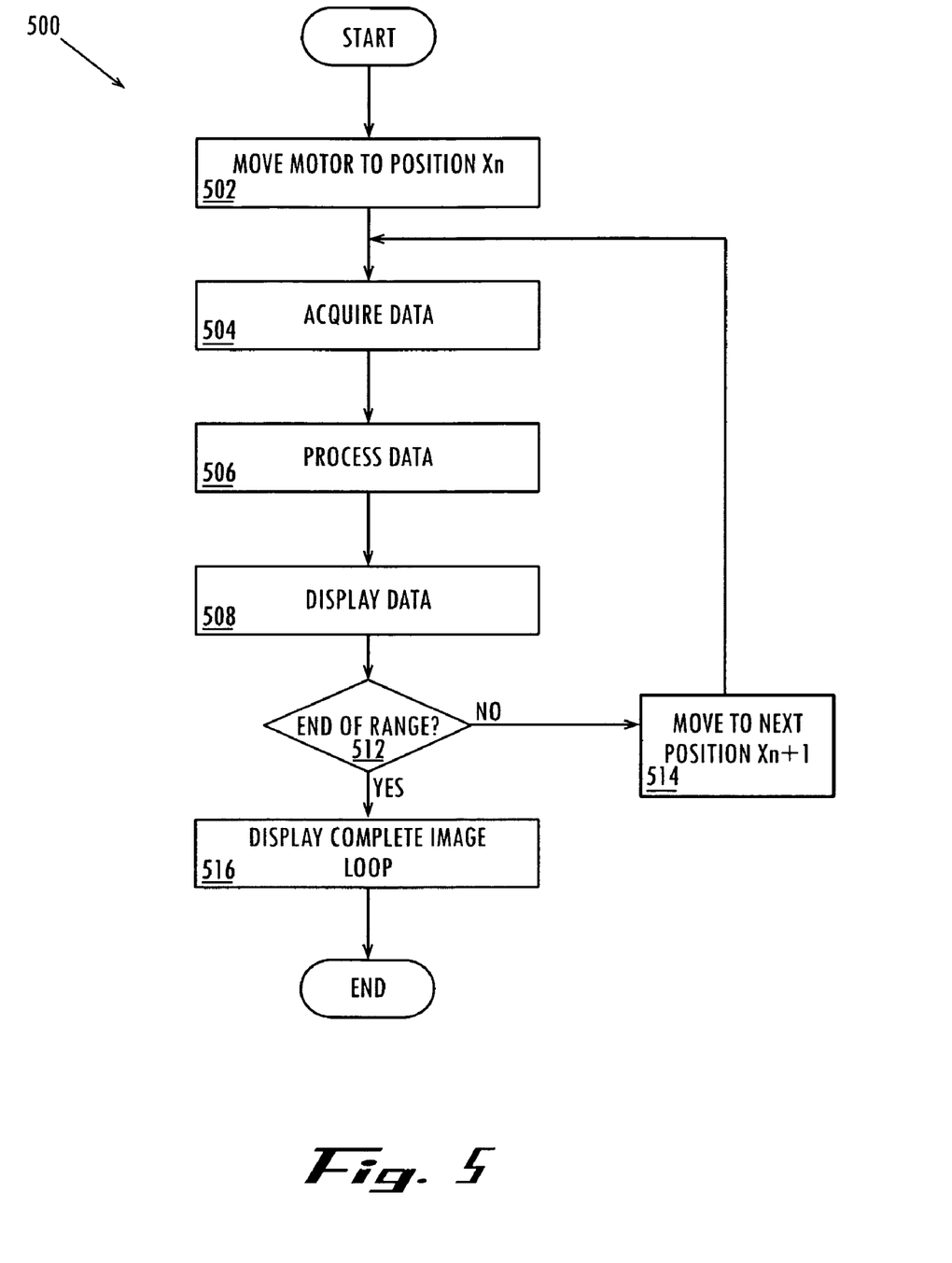
FIG. 5 is flowchart illustrating the overall operation of the system for producing an ultrasound image using line based image reconstruction.
Figure 6:
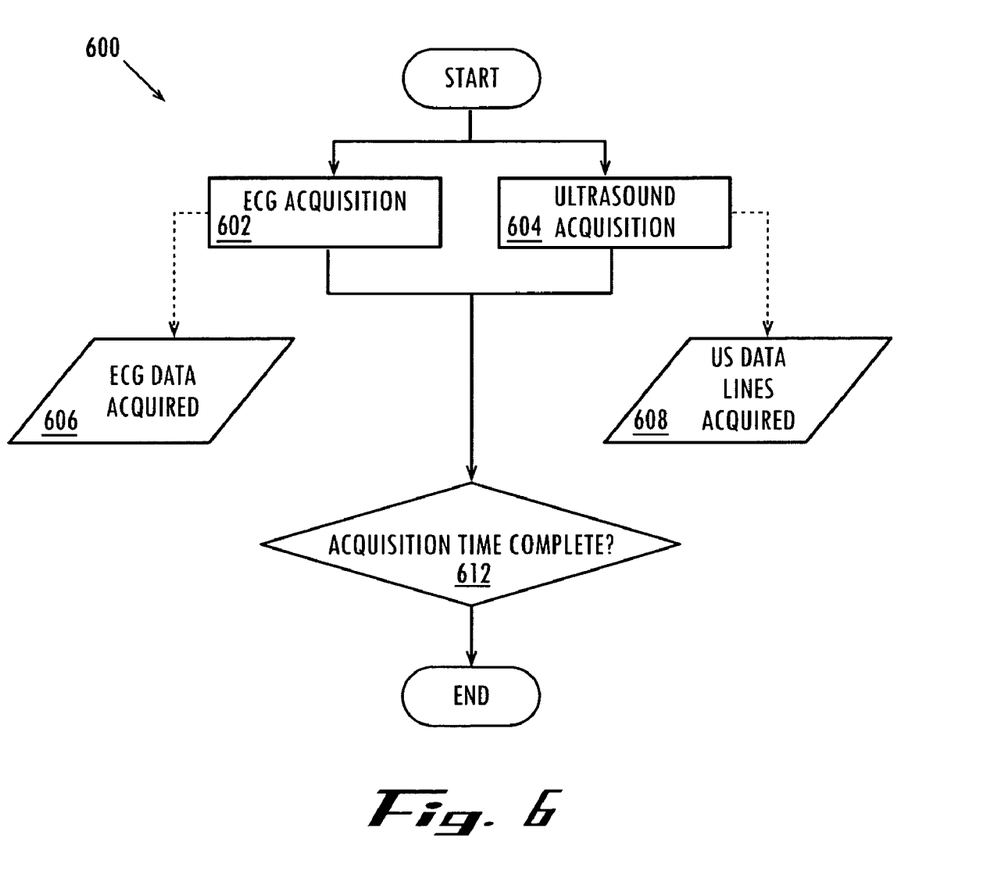
FIG. 6 is a flowchart illustrating the operation of the acquisition block of FIG. 5.
Figure 7:
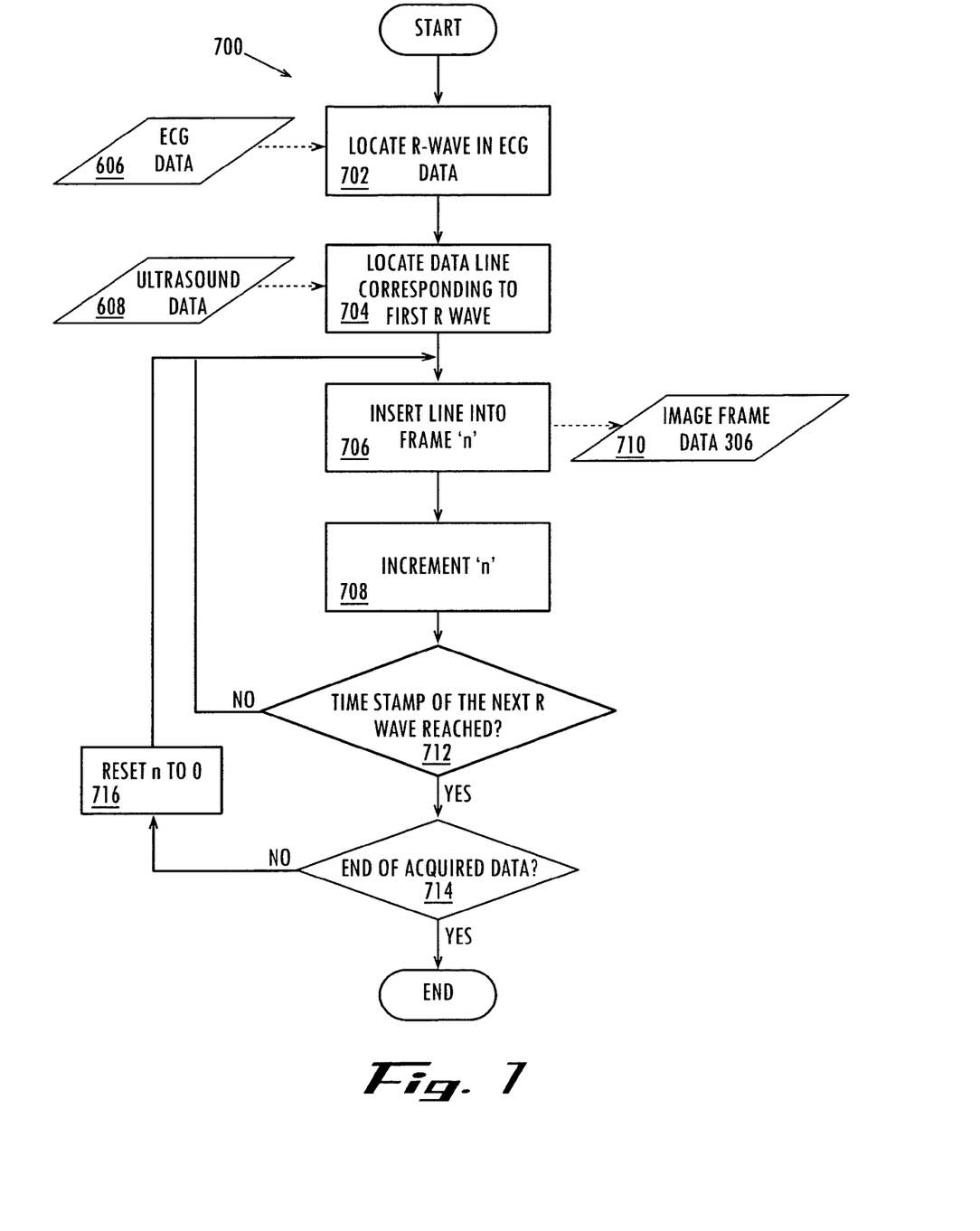
FIG. 7 is a flowchart illustrating the operation of the process data block of FIG. 5.

FIGS. 5, 6 and 7 are flowcharts collectively illustrating the operation of the system for producing an ultrasound image using line based image reconstruction. The blocks in the flowcharts may be executed in the order shown, out of the order shown, or concurrently.

FIG. 5 is flowchart 500 illustrating the overall operation of the system for producing an ultrasound image using line based image reconstruction. In block 502, the transducer in the probe 112 is registered at its home position at one end of its travel. The movement of the transducer 112 is described in commonly assigned, co-pending U.S. patent application Ser. No. 10/683,890, entitled "High Frequency, High Frame-Rate Ultrasound Imaging System, filed on Oct. 10, 2003, which is incorporated herein by reference. In block 504, ultrasound data is acquired for the probe location described in block 502 and stored in memory 121 (FIG. 1). The operation of block 504 will be described in greater detail in FIG. 6.

In block 506, the data acquired in block 504 is processed. The operation of block 506 will be described in greater detail in FIG. 7.

In block 508, the data acquired in block 504 and processed in block 506 is displayed. In block 512 it is determined whether the probe 112 has reached the end of its travel, or sweep. If the probe 112 has not reached the end of its travel, its position is incremented in block 514 and the process returns to block 504 and data acquisition continues. If, in block 512 it is determined that the probe 112 has reached the end of its travel, then, in block 516, a line based reconstructed image is displayed on display 116 as what is referred to as a "B mode" loop.

FIG. 6 is a flowchart 600 illustrating the operation of the acquisition block 504 of FIG. 5. In block 602 ECG data is acquired and stored in memory 121 in block 606. In block 604, ultrasound data is acquired and stored in memory 121 in block 608. Each line 304 (FIG. 3A and FIG. 3B) of ultrasound data is stored in block 608. The ultrasound signal includes the data associated with a scan line and also includes a spatial registration signal associated with the scan line. The ultrasound signal containing the raw data and the spatial registration information is identified with the time stamp by the receive subsystem 120.

In block 612 ECG and ultrasound data acquisition is continued for a period of time specified by a user of the system. The time period specified in block 612 determines the number of ultrasound data lines 304 (FIGS. 3A and 3B) are acquired at a particular probe position. A sufficient amount of data is obtained when at least one heart cycle of data has been collected. Collecting data over more than one heart cycle improves the accuracy of the image.

FIG. 7 is a flowchart 700 illustrating the operation of the process data block 506 of FIG. 5. In block 702, the ECG data stored in block 606 (FIG. 6) is scanned to locate the first specific point 324 in the R wave (326a and 326b) as shown in FIG. 3B as described above. This automatically detects a point in time which is used as the origin for relative ECG time stamps for each element of raw data associated with each can line. Once the peak 324 is located, a corresponding point in the ultrasound data stored in block 608 is located in block 704. In block 706, each line 304 of ultrasound data following this point is placed, in block 710, into a reconstructed frame 306 (FIGS. 3C and 3D) based on its time displacement from the peak 324. For example, a line 304 acquired Tn milliseconds after the peak 324 will be placed into frame Tn.

In block 712 it is determined whether the peak 324 of the next R wave has been reached. If the peak 324 of the next R wave has not been reached, the process returns to block 706. If, in block 712 it is determined that the next peak 324 has been reached, then, in block 714, it is determined whether there is any additional data to process. If there is additional data to process, the image reconstruction subsystem 129 resets its time counter in block 716. If, in block 714 it is determined that there is no additional data to process, then the process ends.

Figure 8:
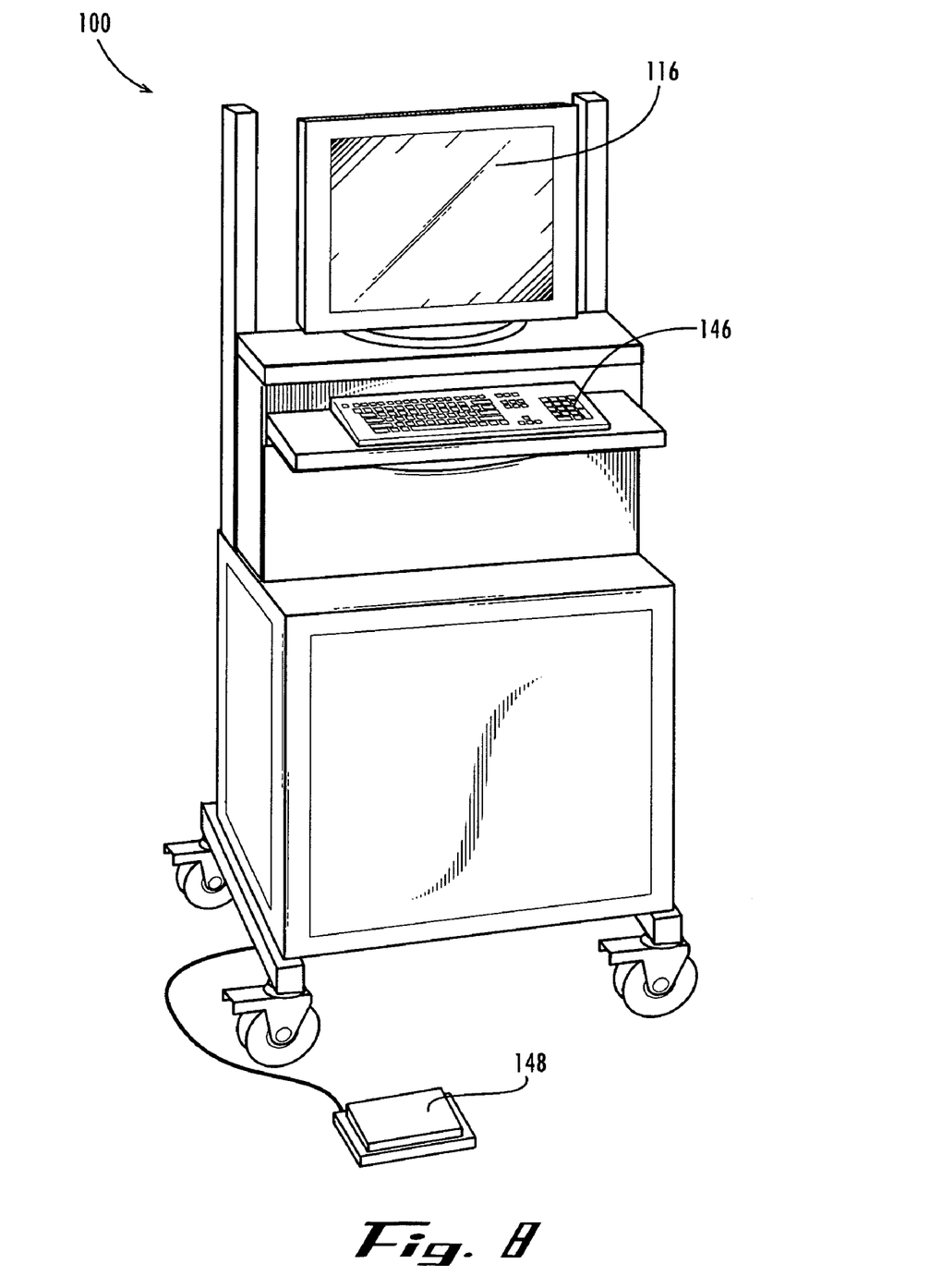
FIG. 8 is a schematic view of an ultrasound system of FIG. 1.

Referring to FIG. 8, an embodiment of the ultrasound system 100 is shown by way of example only. In this example, the ultrasound system 100 is a free-standing unit on casters for mobility. The human machine interface 136 includes a display 116, a keyboard 146, and a foot control 148. The control subsystem 127 and related components are located inside a case.

Figure 9:
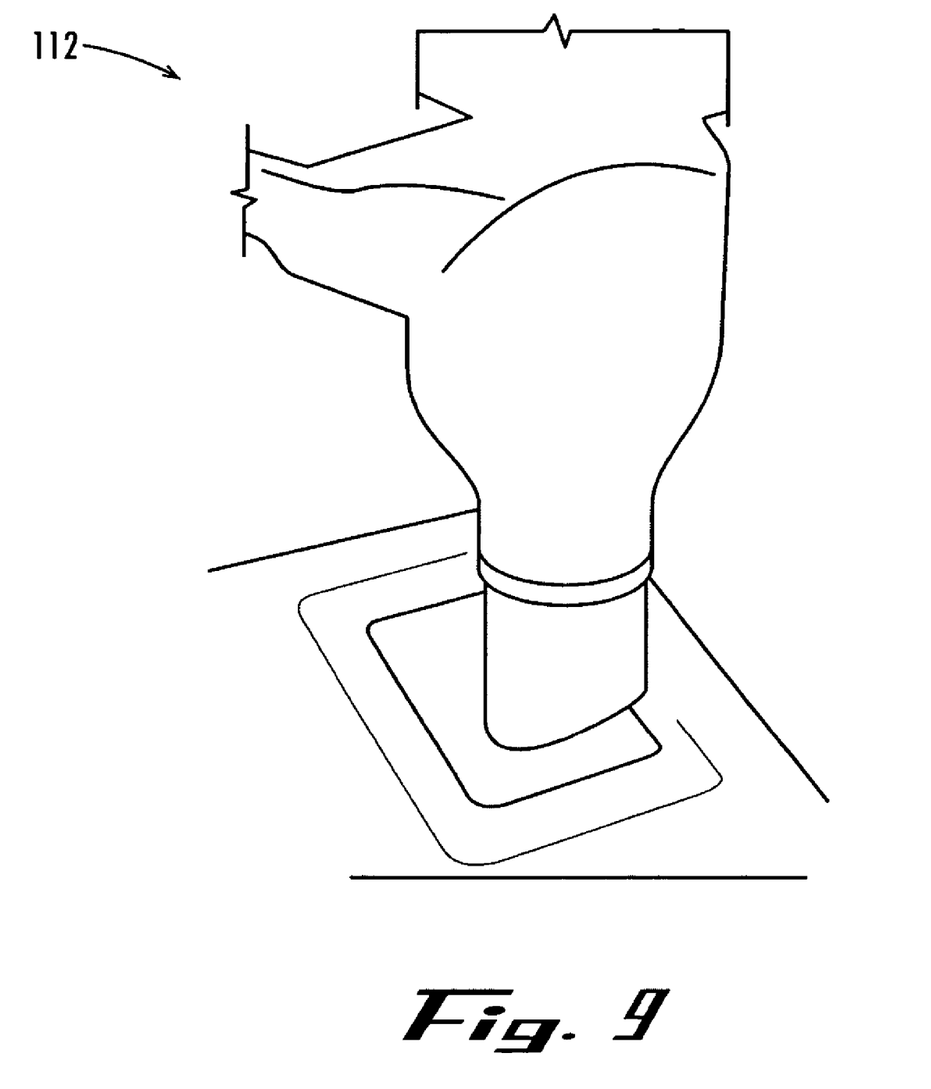
FIG. 9 is a schematic view of an ultrasound scanhead of FIG. 1.

Referring to FIG. 9, an embodiment of the ultrasound probe 112 is shown by way of example only. The purpose of the ultrasound probe 112 is to generate and receive ultrasound signals, and feed these signals back to the ultrasound system 131, with position registration of each of the scan lines containing the raw data.

The ultrasound probe 112, also referred to as a scan head comprises a piezoelectric element(s) to convert ultrasound pressure waves to electrical signals, and received ultrasound pressure waves to electrical signals, and a mechanism to reposition (and record spatial location of) the ultrasound beam. In one embodiment, the positioning mechanism comprises an optical position encoder connected to a high resolution stepping motor as described in commonly assigned, copending U.S. patent application Ser. No. 10/683,890, entitled "High Frequency, High Frame-Rate Ultrasound Imaging System," filed on Oct. 10, 2003, which is incorporated herein by reference. In another embodiment, the positioning mechanism comprises an array of piezoelectric elements which can be electronically steered using variable pulsing and delay mechanisms. Regardless of the positioning mechanism used, the position of each scan line is determined and associated with each scan line as described in FIG. 1.

Figure 10:
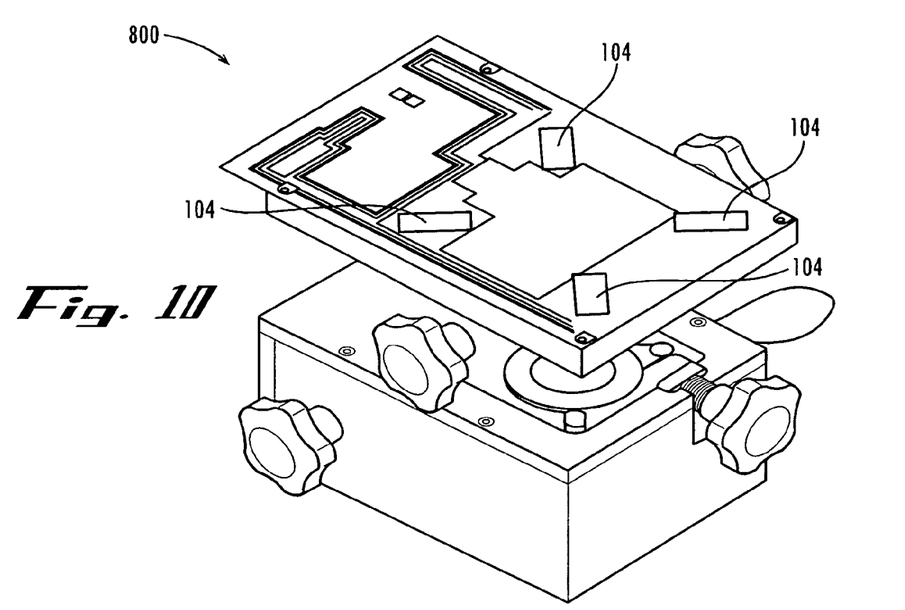
FIG. 10 is a schematic view of the electrodes of FIG. 1.
Figure 11:
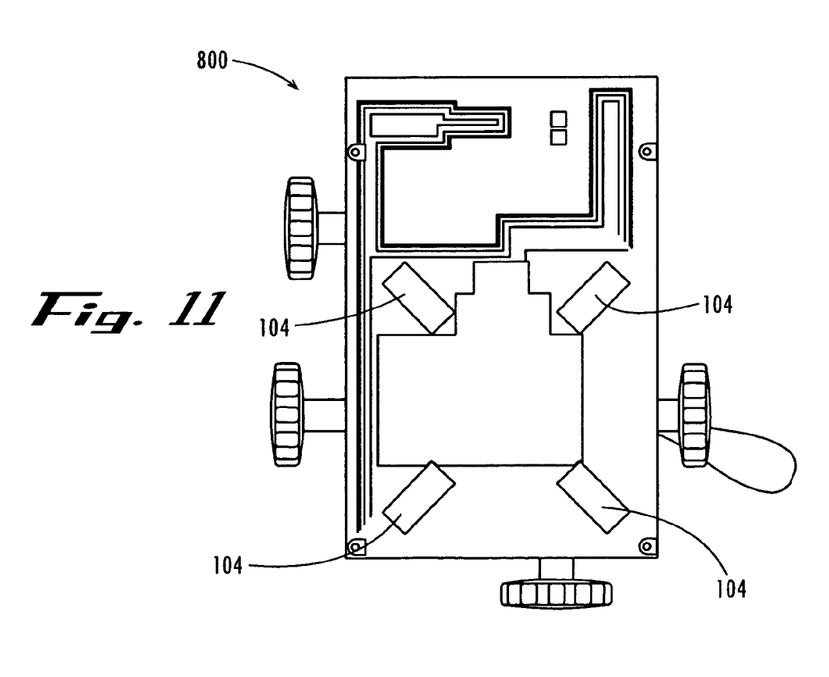
FIG. 11 is a plan view of FIG. 10.

Referring to FIGS. 10 and 11, an embodiment of an ECG apparatus 800 is shown in more detail. The ECG apparatus comprises ECG electrodes 104, and an ECG amplifier 106 (FIG. 1). The ECG amplifier 106 is typically located close to the ECG electrodes 104 (FIG. 1) in a control module (not shown) which also controls a small animal heating element (not shown).

The embodiment of FIGS. 10 and 11 illustrates an example of a set of ECG electrodes designed to collect ECG signals from an adult mouse. Furthermore, knobs (not shown) are provided to adjust the position of the platform as required in various procedures. A control provides a quick height adjustment for the platform. A knob operates a magnet for holding the platform in position and allowing a quick release for coarse positioning of the platform.

Since the strength of the ECG signal obtained from a small animal is weak, the signal is amplified prior to being transmitted to the ultrasound system.

By accurately registering the position of the probe 112 for each scan line, the time of acquisition of each scan line relative to a reference point in the ECG trace 322 (FIG. 3B), each scan line having a raw data element, an effective frame rate at or in excess of 200 frames per second can be achieved during playback of a fully reconstructed data set. An ultrasound system constructed in accordance with the invention records both position registration with respect to the probe 112 and time registration with respect to the scan line relative to the ECG cycle, thus identifying each raw data element. The raw data elements are then used to construct a high precision high frame rate image.

First implementations have demonstrated the capability to acquire image sequences with complete data independence at for example 1000 frames per second. It is anticipated that operations may be performed at much higher frame rates. The frame rate may be as high as the pulse repetition frequency (PRF) limit for any given ultrasound line. The PRF limits the maximum image depth. The maximum image depth is equal to the speed of sound divided by twice the PRF (i.e. speed of sound/(2*PRF)). It is anticipated that this could be as high as approximately 100,000 frames per second.

It will therefore be recognized that a control subsystem has been provided which coordinates the acquisition of raw data (ultrasound lines or "A-Scans") ensuring that data is acquired at each spatial location, for each time window relative to the ECG signal.

Furthermore, an image construction subsystem (or scan converter) has been provided which is capable of reconstructing a sequence of spatially complete image frames at each time window relative to the ECG signal.

Although the invention has been described with reference to certain specific embodiments, various modifications thereof will be apparent to those skilled in the art without departing from the scope of the invention as outlined in the claims appended hereto.

What is claimed is:

1. A method for producing an ultrasound image, comprising:
generating ultrasound at a frequency of at least 20 megahertz (MHz);
transmitting ultrasound at a frequency of at least 20 MHz into a subject;
receiving ultrasound from the subject, wherein the steps of transmitting and receiving are incrementally repeated from a first scan line position through an nth scan line position;
generating a plurality of scan lines at each scan line position, each scan line being offset in time from a reference point of an ECG rhythm; and
processing the received ultrasound to provide an image having an effective frame rate of at least 200 frames per second (fps) using scan line based image reconstruction, wherein the scan based image reconstruction comprises assembling the plurality of scan lines based on the scan line position and the point of time offset from the reference point to form an image frame.

2. The method of claim 1, further comprising generating ultrasound in a frequency range of about 20 MHz to 60 MHz.

3. The method of claim 1, further comprising using the ultrasound on a small animal to image rapidly moving anatomy.

4. The method of claim 3, wherein the small animal is a mouse.

5. The method of claim 1, further comprising using the ultrasound on a small animal to image blood flow.

6. The method of claim 5, wherein the small animal is a mouse.

7. The method of claim 1, further comprising:
repeating the step of processing to form a plurality of image frames at select times offset from the reference point relative to the ECG rhythm.

8. The method of claim 7, further comprising:
time sequencing the plurality of image frames to form a sequence of image frames relative to the ECG rhythm.

9. A system for developing an ultrasound image, comprising:
a scan head having a transducer capable of generating ultrasound energy at a frequency of at least 20 megahertz (MHz);
a transmit subsystem configured to incrementally transmit ultrasound at a first scan position through an nth scan position and to generate a plurality of scan lines at each scan position, each scan line being offset in time from a reference point of an ECG rhythm; and a processor for receiving ultrasound energy and for generating an ultrasound image at an effective frame rate of at least 200 frames per second (fps) using scan line based image reconstruction, wherein the processor is further configured to assemble the plurality of scan lines based on the scan line position and the point in time offset from the reference point to form an image frame.

10. The system of claim 9, wherein the ultrasound occurs at a frequency range of about 20 MHz to 60 MHz.

11. The system of claim 10, wherein the processor is further configured to generate a plurality of image frames at select times from the reference point relative to the ECG rhythm.

12. The system of claim 11 wherein the processor is further configured to time sequence the plurality of image frames relative to the ECG rhythm.

13. The system of claim 9, wherein the ultrasound is performed on a small animal to image rapidly moving anatomy.

14. The system of claim 9, wherein the ultrasound is performed on a small animal to image blood flow.

15. A system for producing an ultrasound image, comprising:

means for generating ultrasound at a frequency of at least 20 megahertz (MHz);

means for transmitting ultrasound at a frequency of at least 20 MHz into a subject;

means for receiving ultrasound from the subject, wherein the means for transmitting ultrasound and the means for receiving ultrasound are incrementally repeated from a first scan line position through an nth scan line position;

means for generating a plurality of scan lines at each scan line position, each scan line being offset in time from a reference point of an ECG rhythm; and means for processing the received ultrasound to provide an image having an effective frame rate of at least 200 frames per second (fps) using scan line based image reconstruction, wherein the scan based image reconstruction comprises means for assembling the plurality of scan lines based on the scan line position and the point of time offset from the reference point to form an image frame.

16. The system of claim 15, further comprising means for generating ultrasound in a frequency range of about 20 MHz to 60 MHz.

17. The system of claim 15, further comprising means for forming a plurality of image frames at select times offset from the reference point of the ECG rhythm.

18. The system of claim 17, further comprising means for time sequencing the plurality of image frames to form a sequence of image frames relative to the ECG rhythm.

19. A method for producing an ultrasound image, comprising:

generating ultrasound in a frequency range of 20–60 megahertz (MHz);

transmitting the ultrasound into a small animal;

receiving the ultrasound from the small animal, wherein the steps of transmitting and receiving are incrementally repeated from a first scan line position through an nth scan line position;

processing the received ultrasound to provide an image having an effective frame rate of at least 200 frames per second (fps) using scan line based image reconstruction to image rapidly moving anatomy, wherein the processing further comprises:

generating a plurality of scan lines at each scan line position, each scan line being offset in time from a reference point of an ECG rhythm; and assembling the plurality of scan lines based on the scan line position and the point in time offset from the reference point to form an image frame.

20. A method for producing an ultrasound image, comprising:

generating ultrasound in a frequency range of 20–60 megahertz (MHz);

transmitting the ultrasound into a small animal;

receiving the ultrasound from the small animal, wherein the steps of transmitting and receiving are incrementally repeated from a first scan line position through an nth scan line position;

processing the received ultrasound to provide an image having an effective frame rate of at least 200 frames per second (fps) using scan line based image reconstruction to image blood flow, wherein the processing further comprises:

generating a plurality of scan lines at each scan line position, each scan line being offset in time from a reference point of an ECG rhythm; and assembling the plurality of scan lines based on the scan line position and the point in time offset from the reference point to form an image frame.

21. A system for developing an ultrasound image, comprising:

a scan head having a transducer capable of generating ultrasound energy in a frequency range of 20–60 megahertz (MHz);

a processor for receiving ultrasound energy and for generating an ultrasound image at an effective frame rate of at least 200 frames per second (fps) using scan line based image reconstruction;

a transmit subsystem configured to incrementally transmit ultrasound at a first scan position through an nth scan position and to generate a plurality of scan lines at each scan line position, each scan line being offset in time from a reference point of an ECG rhythm; and an image reconstruction subsystem configured to assemble the plurality of scan lines based on the scan line position and the point in time offset from the reference point to form an image frame.

22. The system of claim 21, wherein the image reconstruction subsystem is further configured to form a plurality of image frames at select times offset from the reference point relative to the ECG rhythm.

23. The system of claim 22, wherein the image reconstruction subsystem is further configured to time sequence the plurality of image frames to form a sequence of image frames relative to the ECG rhythm.

24. A system for producing an ultrasound image, comprising:

means for generating ultrasound in a frequency range of 20–60 megahertz (MHz);

means for transmitting the ultrasound into a subject;

means for receiving ultrasound from the subject, wherein the means for transmitting ultrasound and the means for receiving ultrasound are incrementally repeated from a first scan line position through an nth scan line position;

means for processing the received ultrasound to provide an image having an effective frame rate of at least 200 frames per second (fps) using scan line based image reconstruction, wherein the means for processing comprises:

means for generating a plurality of scan lines at each scan line position, each scan line being offset in time from a reference point of an ECG rhythm; and means for assembling the plurality of scan lines based on the scan line position and the point in time offset from the reference point to form an image frame.

25. The system of claim 24, further comprising means for forming a plurality of image frames at select times offset from the reference point relative to the ECG rhythm.

26. The system of claim 25, further comprising means for time sequencing the plurality of image frames to form a sequence of image frames relative to the ECG rhythm.

* * * * *